(12) United States Patent
Asai

(10) Patent No.: US 11,241,210 B2
(45) Date of Patent: Feb. 8, 2022

(54) RADIATION IMAGE CAPTURING APPARATUS AND RADIATION IMAGE CAPTURING SYSTEM

(71) Applicant: CANON KABUSHIKI KAISHA, Tokyo (JP)

(72) Inventor: Hiroki Asai, Kawasaki (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 16/821,534

(22) Filed: Mar. 17, 2020

(65) Prior Publication Data
US 2020/0305823 A1    Oct. 1, 2020

(30) Foreign Application Priority Data

Mar. 29, 2019  (JP) .............................. JP2019-068067

(51) Int. Cl.
*A61B 6/00* (2006.01)
*H05G 1/60* (2006.01)
*H04N 5/32* (2006.01)

(52) U.S. Cl.
CPC ................ *A61B 6/52* (2013.01); *A61B 6/563* (2013.01); *H05G 1/60* (2013.01); *H04N 5/32* (2013.01)

(58) Field of Classification Search
CPC .. A61B 6/00; A61B 6/52; A61B 6/563; A61B 6/44; A61B 6/4429; A61B 6/54; A61B 6/542; A61B 6/56; A61B 6/566; H05G 1/60; H04N 5/32

See application file for complete search history.

(56) References Cited

U.S. PATENT DOCUMENTS

| 9,921,319 | B2 | 3/2018 | Asai et al. |
| 10,055,819 | B2 | 8/2018 | Asai |
| 10,371,647 | B2 | 8/2019 | Asai |
| 10,539,684 | B2 | 1/2020 | Asai et al. |
| 2005/0169425 | A1 | 8/2005 | Takasawa |
| 2018/0180751 | A1 | 6/2018 | Asai et al. |
| 2018/0275075 | A1 | 9/2018 | Tamura et al. |
| 2020/0359978 | A1* | 11/2020 | Okada ..................... A61B 6/542 |

FOREIGN PATENT DOCUMENTS

| JP | 2014-012109 A | 1/2014 |
| JP | 2016-171917 | 9/2016 |

* cited by examiner

*Primary Examiner* — Jurie Yun
(74) *Attorney, Agent, or Firm* — Venable LLP

(57) ABSTRACT

A radiation image capturing apparatus is provided. The apparatus comprises an image capturing unit configured to acquire a radiation image, the image capturing unit being provided with a plurality of receptor fields for acquiring irradiation information of radiation concerning an integrated dose of radiation entering during irradiation with radiation, and a selection unit configured to select a receptor field, of the plurality of receptor fields, which is used by a user. The selection unit changes an upper limit of the number of receptor fields, of the plurality of receptor fields, which are used for one image capturing operation depending on when the radiation image capturing apparatus is attached to a stand to which the radiation image capturing apparatus can be attached and when the radiation image capturing apparatus is detached from the stand.

20 Claims, 8 Drawing Sheets

FIG. 11

| IF | SETTING |
|---|---|
| RADIATION IMAGE CAPTURING APPARATUS 1 IF | FLUOROSCOPIC TABLE |
| RADIATION IMAGE CAPTURING APPARATUS 2 IF | FREE POSITION |
| RADIATION IMAGE CAPTURING APPARATUS 3 IF | STANDING POSITION STAND |
| ACCESS POINT IF | FREE POSITION |

RADIATION IMAGE CAPTURING APPARATUS AND RADIATION IMAGE CAPTURING SYSTEM

BACKGROUND OF THE INVENTION

Field of the Invention

The present invention relates to a radiation image capturing apparatus and a radiation image capturing system.

Description of the Related Art

In medical image diagnosis and non-destructive examination, a radiation image capturing apparatus using an FPD (Flat Panel Detector) formed from a semiconductor material has been widely used. Such a radiation image capturing apparatus is known to measure radiation entering the radiation image capturing apparatus in real time. Detecting a radiation dose in real time can grasp the integrated dose of radiation entering during irradiation with radiation and perform AEC (Automatic Exposure Control). Some radiation image capturing apparatus has a plurality of detection ranges (to be referred to as receptor fields hereinafter) set for AEC. Japanese Patent Laid-Open No. 2016-171917 discloses a technique of calculating relative position information concerning an X-ray tube and an FPD by using a tube position detection unit provided for an X-ray tube suspension unit that supports an X-ray tube and an FPD position detection unit arranged in an image capturing table such as a stand unit or supine position table. This technique can calculate, from the calculated relative position information, a specific position on the FPD at which X-rays are applied, set some of a plurality of receptor fields which are not included in an X-ray irradiation region as unused receptor fields, and perform AEC by using a receptor field included in the X-ray irradiation region.

SUMMARY OF THE INVENTION

A radiation image capturing apparatus is sometimes detached from a stand such as an image capturing table instead of being attached to the stand to perform image capturing to obtain a radiation image at an arbitrary position by using AEC. Assume that the radiation image capturing apparatus is detached from the stand, and the user selects a receptor field used for AEC. In this case, the positional relationship between an object and a plurality of receptor fields is sometime more difficult to grasp than when the radiation image capturing apparatus is attached to the stand. Japanese Patent Laid-Open No. 2016-171917 discloses nothing about a technique of detaching an FPD from an image capturing table and then performing image capturing. In addition, in the X-ray image capturing apparatus disclosed in Japanese Patent Laid-Open No. 2016-171917, an FPD position detection unit provided on the stand detects the position of the FPD. For this reason, when the radiation image capturing apparatus (FPD) is detached from the stand and used, it is not possible to calculate a specific position on the FPD at which X-rays are applied.

Some embodiments of the present invention provide a technique advantageous in setting a receptor field when performing image capturing by using the AEC function upon detaching the radiation image capturing apparatus from the stand.

According to some embodiments, a radiation image capturing apparatus comprising: an image capturing unit configured to acquire a radiation image, the image capturing unit being provided with a plurality of receptor fields for acquiring irradiation information of radiation concerning an integrated dose of radiation entering during irradiation with radiation; and a selection unit configured to select a receptor field, of the plurality of receptor fields, which is used by a user, wherein the selection unit changes an upper limit of the number of receptor fields, of the plurality of receptor fields, which are used for one image capturing operation depending on when the radiation image capturing apparatus is attached to a stand to which the radiation image capturing apparatus can be attached and when the radiation image capturing apparatus is detached from the stand, is provided.

Further features of the present invention will become apparent from the following description of exemplary embodiments (with reference to the attached drawings).

BRIEF DESCRIPTION OF THE DRAWINGS

FIG. 11 is a view showing an example of a setting information table in the radiation image capturing apparatus in FIG. 10.

DESCRIPTION OF THE EMBODIMENTS

Figure 1:
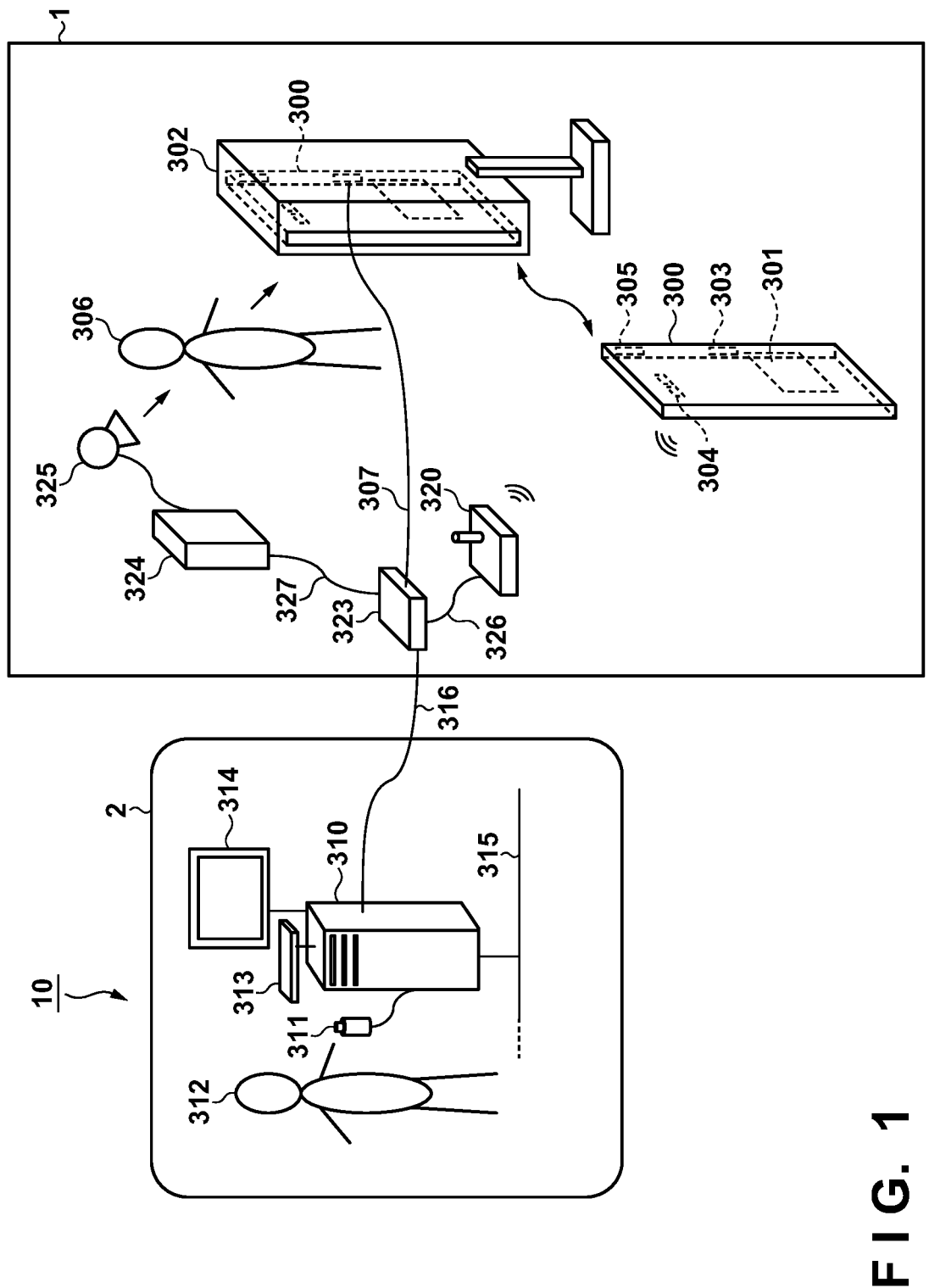
FIG. 1 is a view showing an example of the arrangement of a radiation image capturing system using a radiation image capturing apparatus according to the present invention.

Hereinafter, embodiments will be described in detail with reference to the attached drawings. Note, the following embodiments are not intended to limit the scope of the claimed invention. Multiple features are described in the embodiments, but limitation is not made an invention that requires all such features, and multiple such features may be combined as appropriate. Furthermore, in the attached drawings, the same reference numerals are given to the same or similar configurations, and redundant description thereof is omitted.

Note that radiation according to the present invention can include not only α-rays, βrays, and γ-rays that are beams generated by particles (including photons) emitted by radioactive decay but also beams having energy equal to or higher than the energy of these beams, for example, X-rays, particle rays, and cosmic rays.

A radiation image capturing apparatus according to some embodiments of the present invention will be described with reference to FIGS. 1 to 8. FIG. 1 shows an example of the arrangement of a radiation image capturing system 10 using a radiation image capturing apparatus 300 according to the first embodiment of the present invention.

As shown in FIG. 1, the radiation image capturing system 10 includes a radiation room 1 where a radiation image is obtained by irradiating a subject 306 with radiation and a control room 2 arranged near the radiation room 1. The radiation room 1 is provided with the radiation image capturing apparatus 300, a standing position stand 302, a radiation image capturing apparatus communication cable 307, an access point 320, a communication controller 323, a radiation generator 324, a radiation source 325, an access point communication cable 326, and a radiation generator communication cable 327. The control room 2 is provided with a controller 310, a radiation irradiation switch 311, an input device 313, a display device 314, an in-hospital LAN 315, and a radiation room communication cable 316.

The radiation image capturing apparatus 300 includes a power supply control unit 301 constituted by a battery and the like, a wired communication unit 303, a wireless communication unit 304, and an attachment detection unit 305 for the standing position stand 302. The radiation image capturing apparatus 300 detects the radiation transmitted through the subject 306 and generates radiation image data. The wired communication unit 303 enables exchange of information between the radiation image capturing apparatus 300 and the controller 310 and the like by cable connection using, for example, a communication standard having predetermined protocols or a standard such as Ethernet®. The wireless communication unit 304 includes, for example, an antenna and a circuit board including a communication IC. The circuit board including the communication IC enables exchange of information between the radiation image capturing apparatus 300 and the controller 310 and the like by performing communication processing of protocols based on a wireless LAN or the like through the antenna. Wireless communication is not specifically limited in terms of frequency band, standard, and scheme. For example, a near field communication scheme such as NFC or Bluetooth® or a UWB scheme may be used. In addition, the wireless communication unit 304 is compatible with a plurality of radio communication schemes and may perform communication by selecting one of them as appropriate.

The standing position stand 302 is a stand to which the radiation image capturing apparatus 300 is attached to allow image capturing to obtain a radiation image in a standing position. The radiation image capturing apparatus 300 can be attached and detached to and from the standing position stand 302, and can perform image capturing to obtain radiation images with and without being attached to a stand. The attachment detection unit 305 detects whether the radiation image capturing apparatus 300 is attached to a stand (for example, the standing position stand 302). For example, the attachment detection unit 305 may be a contact type sensor such as a limit switch. Alternatively, the attachment detection unit 305 may be a non-contact type sensor such as an inductive type sensor, capacitance type sensor, or magnetic sensor. Furthermore, the attachment detection unit 305 can be implemented by, for example, receiving a signal for electrically detecting that the radiation image capturing apparatus 300 is attached to a stand when the radiation image capturing apparatus 300 is attached to the stand.

The radiation image capturing apparatus communication cable 307 is a cable for connecting the radiation image capturing apparatus 300 to the communication controller 323. The access point 320 performs wireless communication between the radiation image capturing apparatus 300 and the wireless communication unit 304. For example, when the radiation image capturing apparatus 300 is used upon being detached from the standing position stand 302, the access point 320 can be used to relay communication between the radiation image capturing apparatus 300 and the controller 310 and the radiation generator 324. The arrangement shown in FIG. 1 has exemplified the case in which the radiation image capturing apparatus 300 communicates with the communication controller 323 through the access point 320. However, this is not exhaustive. The radiation image capturing apparatus 300 or the communication controller 323 may function as an access point, and the radiation image capturing apparatus 300 and the communication controller 323 may directly communicate with each other without through the access point 320. The communication controller 323 performs control to enable communication with each of the radiation image capturing apparatus 300, the access point 320, the radiation generator 324, and the controller 310. The access point communication cable 326 is a cable for connecting the access point 320 to the communication controller 323. The radiation generator communication cable 327 is a cable for connecting the radiation generator 324 to the communication controller 323.

The radiation generator 324 controls the radiation source 325 so as to apply radiation based on the irradiation conditions set by a user 312 (for example, a radiation technician). The radiation source 325 irradiates the subject 306 with radiation under the control of the radiation generator 324.

The controller 310 communicates with the radiation generator 324 and the radiation image capturing apparatus 300 through the communication controller 323 and comprehensively controls the radiation image capturing system 10. The radiation irradiation switch 311 inputs the timing of irradiation with radiation in accordance with an operation by the user 312. The input device 313 is a device for inputting an instruction from the user 312, and includes various types of input devices such as a keyboard and a touch panel. The display device 314 is a device for displaying radiation image data having undergone image processing and GUIs, and includes a display. The radiation image capturing apparatus 300 may have functions corresponding to the input device 313 and the display device 314.

The in-hospital LAN 315 is connected to a backbone network in the hospital. The backbone network in the hospital can be, for example, an HIS (Hospital Information System) or RIS (Radiation Information System). The radiation room communication cable 316 is a cable for connecting the controller 310 in the control room 2 to the communication controller 323 in the radiation room 1.

Figure 2:
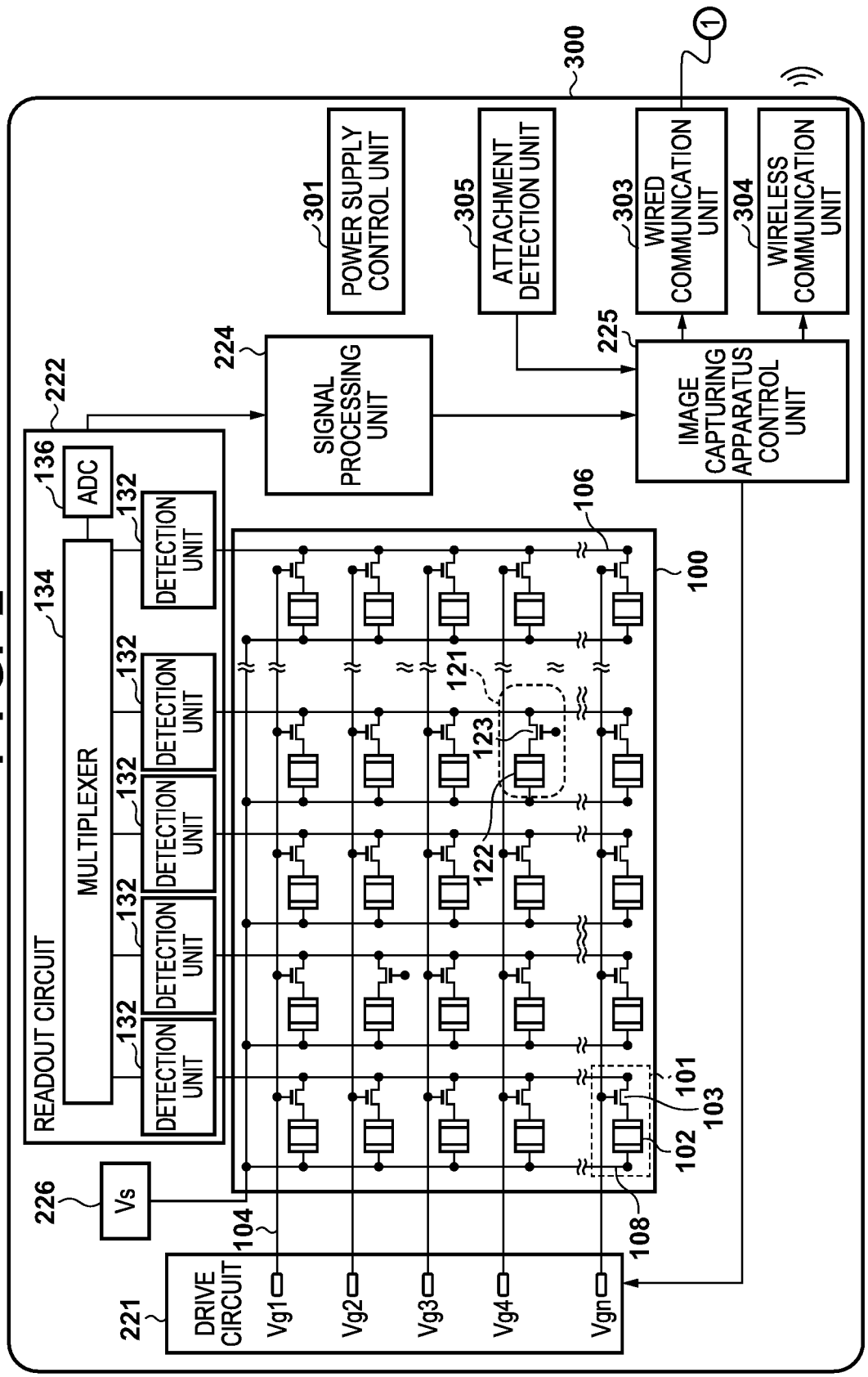
FIG. 2 is a block diagram showing an example of the arrangement of the radiation image capturing apparatus in FIG. 1.

FIG. 2 shows an example of the arrangement of the radiation image capturing apparatus 300. As shown in FIG. 2, the radiation image capturing apparatus 300 has an image capturing unit 100 for capturing a radiation image. The image capturing unit 100 has a function for detecting applied radiation. The image capturing unit 100 has a plurality of pixels arranged to form a plurality of rows and a plurality of columns.

The plurality of pixels include pixels 101 (to be described as detection pixels hereinafter for a description about the application to acquire irradiation information of radiation) for acquiring radiation images or acquiring irradiation information of radiation and correction pixels 121 for removing dark current components and crosstalk components.

Each detection pixel 101 includes a conversion element 102 for converting radiation into an electrical signal and a switch 103 arranged between a column signal line 106 and the conversion element 102. Each conversion element 102 may be constituted by a scintillator for converting radiation into light and a photoelectric conversion element for converting the light converted by the scintillator into an electrical signal. Each scintillator is formed into, for example, a sheet-like member covering the image capturing unit 100, and may be shared by a plurality of pixels. The conversion element 102 may be formed from a conversion element for directly converting radiation into an electrical signal without including any scintillator. Each switch 103 includes, for example, a TFT (Thin-Film Transistor) having an active region formed from a semiconductor such as amorphous silicon or polysilicon.

Each correction pixel 121 includes a conversion element 122 having an arrangement similar to that of the detection pixel 101 and a switch 123. The correction pixel 121 has an arrangement similar to that of the detection pixel 101 but differs in sensitivity with which incident radiation is converted into an electrical signal from the detection pixel 101 to output a different electrical signal with respect to incident radiation. For example, in order to make the detection pixel 101 have higher sensitivity for the detection of radiation than the correction pixel 121, the region of the detection pixel 101 which is used to detect radiation may be made larger than the correction pixel 121. Consider, for example, a pixel that directly converts radiation into an electrical signal. In this case, a shielding member made of a heavy metal such as lead may be provided as a shielding member for shielding against radiation on the conversion element of the correction pixel 121. Consider also an indirect type pixel that converts radiation into light by using a scintillator and then converts the light into an electrical signal. In this case, a shielding film made of aluminum or the like may be provided as a shielding member for shielding against light between the conversion element of the correction pixel 121 and the scintillator. A radiation image capturing apparatus of any conversion type can change the sensitivity with respect to radiation by providing a shielding member in a region overlapping at least part of the conversion element of the correction pixel 121 in orthogonal projection with respect to the image capturing unit 100. This makes it possible to more accurately generate irradiation information of radiation acquired by using the detection pixel 101 by subtraction between the electrical signal obtained from the detection pixel 101 and the electrical signal obtained from the correction pixel 121.

The radiation image capturing apparatus 300 includes a plurality of column signal lines 106 and a plurality of drive lines 104. Each column signal line 106 corresponds to one of the plurality of columns on which pixels in the image capturing unit 100 are arranged. Each drive line 104 corresponds to one of the plurality of rows on which pixels in the image capturing unit 100 are arranged. The drive lines 104 are driven by a drive circuit 221.

One electrode of each conversion element 102 is connected to one main electrode of the switch 103, and the other electrode of the conversion element 102 is connected to a bias line 108. Likewise, one electrode of each conversion element 122 is connected to one main electrode of the switch 123, and the other electrode of the conversion element 122 is connected to the bias line 108.

Each bias line 108 receives a bias voltage Vs from an element power supply circuit 226. The bias line 108 is commonly connected to the other electrode of the conversion element 102 and the other electrode of the conversion element 122. The bias voltage Vs is supplied from the element power supply circuit 226. The power supply control unit 301 is constituted by a battery, a DCD converter, and the like. The power supply control unit 301 includes the element power supply circuit 226 and generates analog circuit power and digital circuit power for drive control and communication.

The main electrodes of the switches 103 of the detection pixels 101 and the switches 123 of the correction pixels 121 constituting one column are connected to one column signal line 106. The control electrodes of the switches 103 of the detection pixels 101 and the switches 123 of the correction pixels 121 constituting one row are connected to one drive line 104. The plurality of column signal lines 106 are connected to a readout circuit 222. In this case, the readout circuit 222 includes a plurality of detection units 132, a multiplexer 134, and an AD (Analog Digital) converter 136.

Each of the plurality of column signal lines 106 is connected to a corresponding one of the plurality of detection units 132 of the readout circuit 222. In this case, one column signal line 106 corresponds to one detection unit 132. The detection unit 132 includes, for example, a differential amplifier. The multiplexer 134 selects the plurality of detection units 132 in a predetermined order and supplies a signal from the selected detection unit 132 to the AD converter 136. The AD converter 136 converts the supplied signal into a digital signal and outputs it.

A signal processing unit 224 outputs information indicating irradiation of the radiation image capturing apparatus 300 with radiation based on an output from the readout circuit 222 (AD converter 136). More specifically, the signal processing unit 224 performs characteristic correction processing of removing dark current components and crosstalk components in the radiation image capturing apparatus 300 by using the correction pixels 121, detection of irradiation with radiation, calculation of the irradiation dose of radiation and an integrated dose, and the like.

An image capturing apparatus control unit 225 controls the drive circuit 221, the readout circuit 222, and the like based on information from the signal processing unit 224 and a control command from the controller 310.

Figure 3:
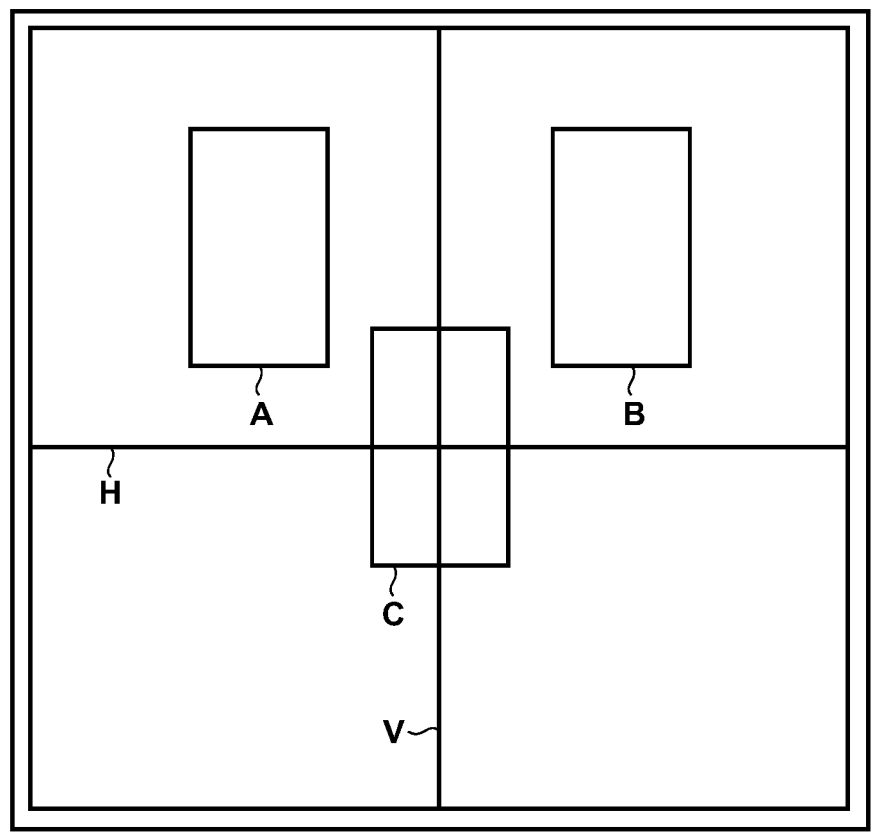
FIG. 3 is a view showing an example of the layout of receptor fields of the radiation image capturing apparatus in FIG. 1.
Figure 4:
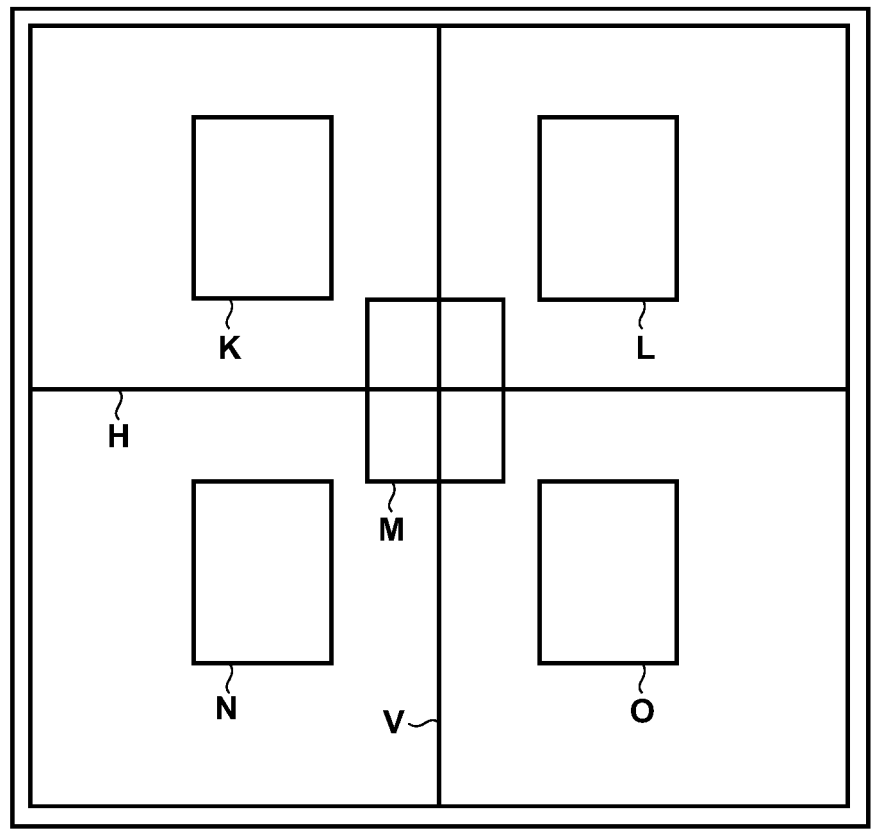
FIG. 4 is a view showing an example of the layout of receptor fields of the radiation image capturing apparatus in FIG. 1.

The image capturing unit 100 is provided with a plurality of receptor fields including the detection pixels 101 and the correction pixels 121 to acquire irradiation information of radiation by performing automatic exposure. Receptor fields are arranged in regions such as those shown in FIGS. 3 and 4 like a separate AEC sensor. FIG. 3 shows the image capturing unit 100 provided with three receptor fields including a receptor field A, a receptor field B, and a receptor field C. FIG. 4 shows the image capturing unit 100 provided with five receptor fields including a receptor field K, a receptor field L, a receptor field M, a receptor field N, and a receptor field O. The numbers and layouts of receptor fields are not limited to them. For example, the image capturing unit 100 may be provided with two, four, and six or more receptor fields. In addition, regions in which receptor fields are arranged may be set as appropriate.

Figure 5:
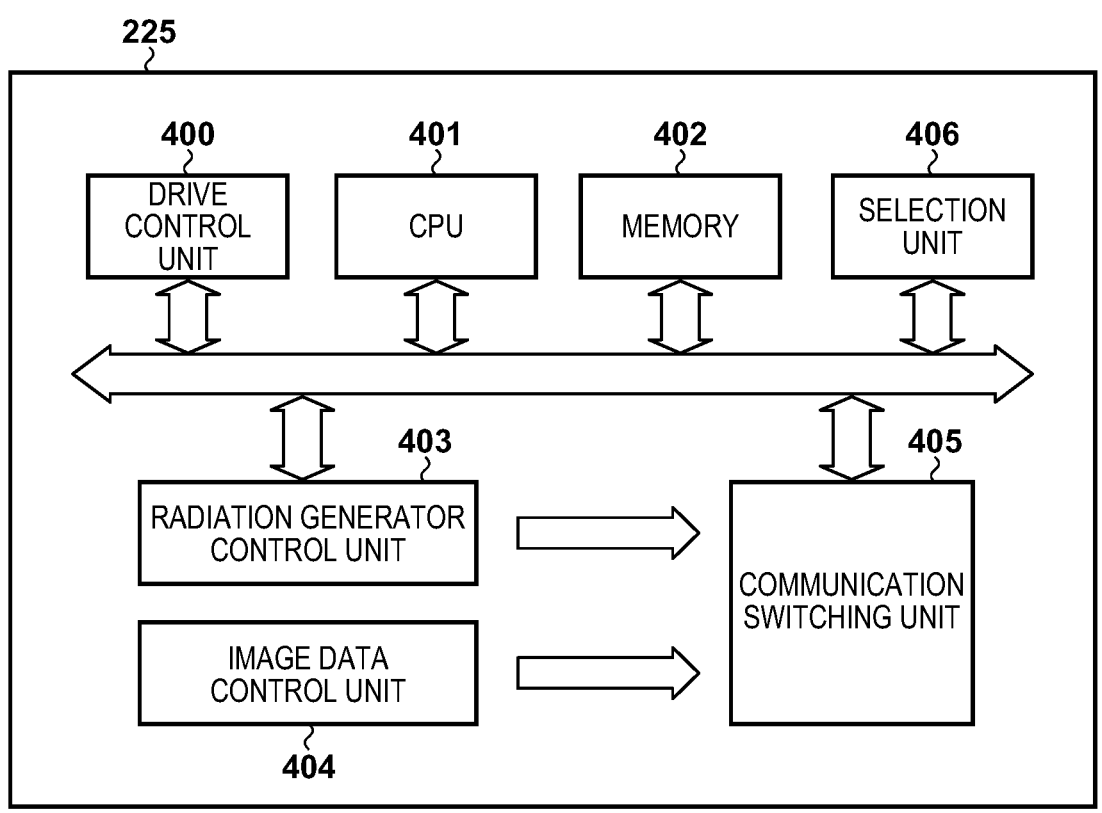
FIG. 5 is a block diagram showing an example of the arrangement of the control unit of the radiation image capturing apparatus in FIG. 1.

FIG. 5 shows an example of the arrangement of the image capturing apparatus control unit 225 of the radiation image capturing apparatus 300. As shown in FIG. 5, the image capturing apparatus control unit 225 includes a drive control unit 400, a CPU 401, a memory 402, a radiation generator control unit 403, an image data control unit 404, a communication switching unit 405, and a selection unit 406.

The drive control unit 400 controls the drive circuit 221 and the readout circuit 222 based on information input from the signal processing unit 224 and commands input from the controller 310. The CPU 401 controls the overall radiation image capturing apparatus 300 by using programs and various types of data stored in the memory 402. For example, the memory 402 stores programs and various types of data used when the CPU 401 executes processing. Various types of data include data obtained by processing by the CPU 401 and radiation image data. The radiation generator control unit 403 controls communication with the radiation generator 324 based on information input from the signal processing unit 224 and information input from the drive control unit 400. The radiation generator control unit 403 exchanges information concerning control of the radiation generator (for example, the start of irradiation with radiation, the notification of stoppage, the irradiation dose of radiation, and an integrated irradiation dose) with the radiation generator 324. The image data control unit 404 saves image data from the readout circuit 222 in the memory 402 and controls communication with the controller 310. The image data control unit 404 exchanges information concerning radiation image data and control (for example, control commands) with the controller 310. The communication switching unit 405 switches the communication unit so as to activate communication by the wired communication unit 303 when a wired cable 322 is connected to the radiation image capturing apparatus 300 and to activate communication by the wireless communication unit 304 when the wired cable 322 is disconnected from the radiation image capturing apparatus 300.

The selection unit 406 is provided for the image capturing apparatus control unit 225 to allow the user 312 to select one of the plurality of receptor fields which is to be used for AEC control when performing image capturing to obtain a radiation image by using AEC (Automatic Exposure Control). The selection unit 406 causes the image capturing apparatus control unit 225 to change the upper limit of the number of receptor fields of the plurality of receptor fields which are used for one image capturing operation depending on whether the radiation image capturing apparatus 300 is attached to a stand (for example, the standing position stand 302) to which the radiation image capturing apparatus 300 can be attached or the radiation image capturing apparatus 300 is detached from the stand. The selection unit 406 changes the upper limit of the number of receptor fields of the plurality of receptor fields which are used for one image capturing operation in accordance with, for example, the relationship between the radiation image capturing apparatus 300 and the standing position stand 302 which is detected by the attachment detection unit 305. The selection unit 406 will be described in detail later.

Figure 6:
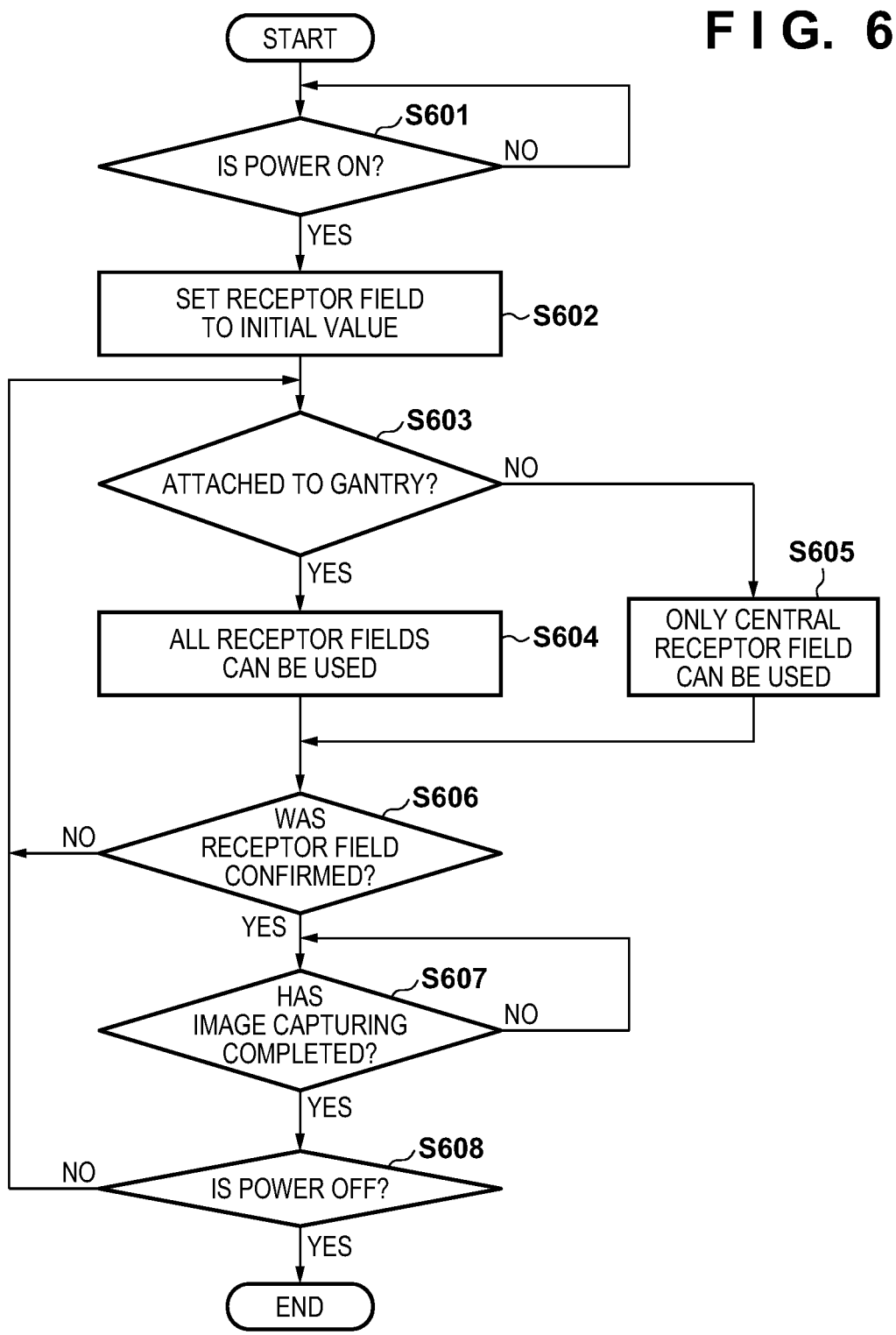
FIG. 6 is a flowchart showing processing at the time of image capturing by the radiation image capturing apparatus in FIG. 1.

The operations of the radiation image capturing apparatus 300 and the radiation image capturing system 10 at the time of performing image capturing to obtain a radiation image by using AEC control will be described next. FIG. 6 is a flowchart at the time of performing image capturing while selecting a receptor field to be used (a radiation detection region (region of interest): ROI) in the radiation image capturing apparatus 300 provided with a plurality of receptor fields for AEC.

Figure 7:
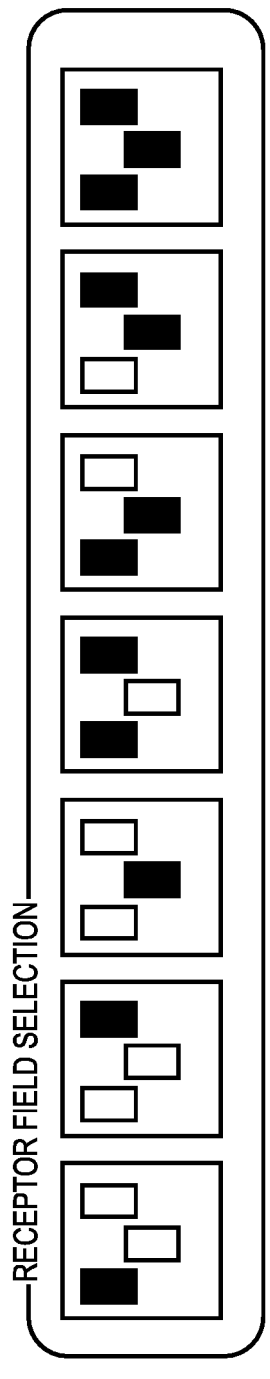
FIG. 7 is a view showing an example of a display screen at the time of setting receptor fields in the radiation image capturing apparatus in FIG. 1.

When the radiation image capturing apparatus 300 is powered on upon powering on of the radiation image capturing system 10, the radiation image capturing system 10 shifts the process from step S601 to step S602. In step S602, initialization is performed such that all the receptor fields in the radiation image capturing apparatus 300 are made settable. In this case, the display device 314 displays to indicate that all the receptor fields set as shown in FIG. 7 are selectable.

The radiation image capturing system 10 then shifts the process to step S603. The user 312 sets information such as the ID, name, and birth date of the subject 306 and image capturing information such as an image capturing region in the controller 310. In this case, the user 312 may set the information of the subject 306 and the image capturing region information by directly inputting them through the input device 313. Alternatively, such information may be automatically set upon selection of an examination order received through the in-hospital LAN 315. Furthermore, the image capturing region information can be set by selecting a preset image capturing protocol.

Upon inputting the information of the subject 306 and the image capturing region information, the user 312 sets the subject 306 and the radiation image capturing apparatus 300 at predetermined positions. At this time, for example, the radiation image capturing apparatus 300 may be detached from the standing position stand 302 or attached to the standing position stand 302. In this manner, the state of the radiation image capturing apparatus 300 may change.

In step S603, when the radiation image capturing apparatus 300 is attached to the standing position stand 302 (YES in step S603), the radiation image capturing system 10 shifts the process to step S604, in which the selection unit 406 makes all the receptor fields selectable. In this case, as shown in FIG. 7, the display device 314 displays to indicate that all the set receptor fields can be simultaneously used for one image capturing operation. The radiation image capturing system 10 then shifts the process to step S606.

In step S603, if the radiation image capturing apparatus 300 is detached from the standing position stand 302 (NO in step S603), that is, the radiation image capturing apparatus 300 is not attached to the standing position stand 302, the radiation image capturing system 10 then advances the process to step S605. In step S605, the selection unit 406 makes only the central receptor field selectable. The radiation image capturing system 10 then shifts the process to step S606. A central receptor field is the one arranged closer to the center than the remaining receptor fields, like the receptor field C in the arrangement shown in FIG. 3 or the receptor field M in the arrangement shown in FIG. 4.

Figure 8:
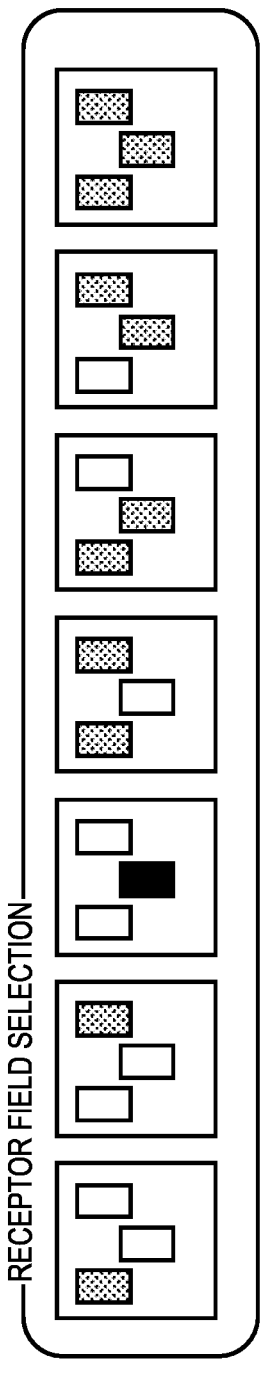
FIG. 8 is a view showing an example of a display screen at the time of setting receptor fields in the radiation image capturing apparatus in FIG. 1.

In step S605, if the selection unit 406 sets only the central receptor field as a selectable receptor field, the selection unit 406 of the radiation image capturing apparatus 300 notifies the controller 310. Upon receiving this notification, the display device 314 displays to indicate that only the central receptor field is a selectable receptor field and the remaining receptor fields are unselectable, as shown in FIG. 8.

In step S606, if the user 312 does not confirm the selection of a receptor field, the process returns to step S603 to periodically repeat the processing from step S603 to step S606. In this manner, the radiation image capturing system 10 may periodically repeatedly determines by a polling scheme whether the radiation image capturing apparatus 300 is attached to the standing position stand 302. Alternatively, for example, the radiation image capturing system 10 may perform interrupt processing in response to a change in the state of a detection signal from the attachment detection unit 305.

When the radiation image capturing apparatus 300 is detached from the standing position stand 302, the selection unit 406 makes only the central receptor field settable for the following reason. When the radiation image capturing apparatus 300 is detached from the standing position stand 302, it is sometimes difficult to align a region of interest of the subject 306, for which the user wants to perform image capturing, with a receptor field for the detection of the irradiation dose of the radiation image capturing apparatus 300. Even in this case, the user 312 can easily visually recognize the central receptor field as a receptor field near the intersection of cross-hairs H and V indicating the center in the longitudinal and lateral directions of the radiation image capturing apparatus 300, and hence can easily perform alignment. In addition, while being detached from the standing position stand 302, the radiation image capturing apparatus 300 is used in an arbitrary direction such as a vertical direction or rotating direction. Even in such a case, the position of a central receptor field is uniquely determined, and hence alignment is facilitated.

In step S606, the user 312 inputs a receptor field among selectable receptor fields which is used for AEC control through the controller 310 in addition to a dose, a maximum irradiation time, a tube current, a tube voltage, region information, and the like. The controller 310 transmits input information such as irradiation conditions for radiation, a region, and receptor fields to the radiation image capturing apparatus 300 and the radiation generator 324. When the user 312 selects a receptor field used for AEC among the selectable receptor fields displayed on the display device 314, the radiation image capturing system 10 shifts the process from step S606 to step S607. Steps S601 to S606 correspond to an image capturing preparation process.

Upon completing image capturing preparation, the user 312 presses the radiation irradiation switch 311. When the user 312 presses the radiation irradiation switch 311, the radiation source 325 irradiates the subject 306 with radiation. In this case, the radiation image capturing apparatus 300 communicates with the radiation generator 324 to control the start of irradiation with radiation. The radiation applied to the subject 306 is transmitted through the subject 306 and enters the radiation image capturing apparatus 300. The radiation image capturing apparatus 300 detects radiation entering a receptor field by the detection pixels 101, and calculates an integrated irradiation dose as the integrated value of doses (attained doses) detected by the signal processing unit 224 in a predetermined period. The image capturing apparatus control unit 225 acquires integrated irradiation dose information from the signal processing unit 224 and a proper dose from region information, image capturing conditions, and the like input by the user 312, and decides the timing of stopping irradiation with radiation. The radiation image capturing apparatus 300 notifies the radiation generator 324 of the stoppage of irradiation with radiation through the radiation image capturing apparatus communication cable 307, the communication controller 323, the radiation generator communication cable 327, and the like based on the decided timing of the stoppage of irradiation with radiation. The radiation generator 324 stops irradiation with radiation based on the notified radiation irradiation stoppage timing. In this embodiment, the radiation image capturing apparatus 300 notifies the stoppage of irradiation with radiation as a result of detection of radiation. However, this is not exhaustive. For example, the radiation image capturing apparatus 300 may transmit an attained dose for each predetermined time as a detection result, and the radiation generator 324 may calculate the integrated dose of attained doses.

Upon stopping irradiation with radiation, the radiation image capturing apparatus 300 acquires the electrical signal generated in accordance with incident radiation. The radiation image capturing apparatus 300 drives the image capturing unit 100 to read out an electrical signal and obtain radiation image data by causing the AD conversion circuit to convert the analog signal into a digital signal. The radiation image capturing apparatus 300 transfers the obtained digital radiation image data to the controller 310 through the radiation image capturing apparatus communication cable 307, the communication controller 323, the radiation generator communication cable 327, and the like.

The controller 310 performs image processing of the received digital radiation image data. The controller 310 displays the radiation image based on the image-processed radiation image data on the display device 314. The controller 310 may function as an image processing apparatus and a display control apparatus.

Upon completion of image capturing, the radiation image capturing system 10 shifts the process from step S607 to step S608, and terminates the processing when the user 312 issues a power-OFF instruction. If no power-OFF instruction is issued, the process returns to step S603.

In this embodiment, the attachment detection unit 305 detects whether the radiation image capturing apparatus 300 is detached from the standing position stand 302. When the radiation image capturing apparatus 300 is detached from the standing position stand 302, the selection unit 406 limits a selectable receptor field to only the central ROI of the radiation image capturing apparatus 300 to facilitate adjusting the positional relationship between the subject 306 and the receptor field used for AEC. This makes it possible to provide the radiation image capturing apparatus 300 and the radiation image capturing system 10 which improve the usability for the user 312 and reduce the load in positioning the subject 306.

In addition, a selectable receptor field is limited to only the central receptor field, and the upper limit of the number of receptor fields used for AEC control in one image capturing operation is reduced. This shortens the period of sampling for the detection of the irradiation dose of radiation and accordingly improves the responsiveness of control on the stoppage of irradiation with radiation, thereby coping with image capturing with a short irradiation time of radiation. This also facilitates image capturing using AEC control in operations other than image capturing with the radiation image capturing apparatus fixed on a stand such as the standing position stand 302. That is, it is possible to provide the radiation image capturing apparatus 300 and the radiation image capturing system 10 which improve the usability for the user 312 and reduce the load in positioning the subject 306. Furthermore, in order to perform image capturing with a short irradiation time of radiation, this system may be configured to make feedback to image capturing conditions such as settings including a tube current and an irradiation time and the distance from the radiation source 325 to the radiation image capturing apparatus 300.

This embodiment has exemplified the arrangement including the standing position stand 302 as a stand included in the radiation image capturing system 10. However, this is not exhaustive. For example, the radiation image capturing system 10 may include a fluoroscopic table and a supine position table as gantries.

This embodiment also has exemplified the case in which the selection unit 406 can select the receptor field of the plurality of receptor fields which is located in the center of the image capturing unit 100. However, this is not exhaustive. This system may be configured to make an arbitrary receptor field selectable in accordance with the region to be captured, image capturing techniques, image capturing conditions, and the like. For example, when the radiation image capturing apparatus 300 is attached to the standing position stand 302 in the arrangement shown in FIG. 3, the selection unit 406 allows the three receptor fields A to C to be simultaneously used for one image capturing operation. In contrast to this, when the radiation image capturing apparatus 300 is detached from the standing position stand 302, the selection unit 406 allows one of the three receptor fields A to C to be used for one image capturing operation. The user 312 may input the position of a receptor field through the input device 313 without being limited to the receptor fields A, B, and C and the receptor fields K, L, M, N, and O set in advance, which are shown in FIGS. 3 and 4.

This embodiment has exemplified the case in which when the radiation image capturing apparatus 300 is detached from the standing position stand 302, the selection unit 406 makes one of the plurality of receptor fields selectable. However, this is not exhaustive. For example, in the arrangement shown in FIG. 4, image capturing may be performed by simultaneously selecting three receptor fields and using them for one AEC control operation.

The radiation image capturing apparatus 300 may further include an extraction unit for extracting a receptor field for automatic exposure from a plurality of receptor fields. When the radiation image capturing apparatus 300 is detached from the standing position stand 302, the extraction unit may extract a selectable receptor field from a plurality of receptor fields and set it as a selectable receptor field in accordance with at least one of an image capturing region, an image capturing technique, and an image capturing condition. For example, in the arrangement shown in FIG. 4, the receptor fields M, L, and O may be extracted as selectable receptor fields in accordance with an image capturing region and the like. In this case, the selection unit 406 decides the number of receptor fields, of the receptor fields M, L, and O, which can be simultaneously used for one image capturing operation in accordance with an image capturing region, an image capturing technique, and an image capturing condition.

This embodiment has exemplified the case in which when the radiation image capturing apparatus 300 is detached from the standing position stand 302, the selection unit 406 reduces the upper limit of the number of receptor fields, of the plurality of receptor fields, which are used for one image capturing operation as compared with a case in which the radiation image capturing apparatus 300 is attached to the standing position stand 302. However, this is not exhaustive. For example, when the attachment detection unit 305 detects that the radiation image capturing apparatus 300 is attached to a stand for image capturing of only a specific region, the selection unit 406 may be controlled to make only a specific one of the plurality of receptor fields selectable.

This embodiment has exemplified the case in which the timing of confirming the selection of a receptor field corresponds to the timing of setting image capturing conditions. However, this is not exhaustive. For example, when an image capturing protocol is selected, for example, a receptor field may be confirmed at another timing.

This embodiment has exemplified the arrangement using a contact type sensor or noncontact type sensor as the attachment detection unit 305. However, this is not exhaustive. For example, the attachment detection unit 305 may detect that the radiation image capturing apparatus 300 is attached to the standing position stand 302, when the radiation image capturing apparatus 300 is connected to the connector provided for the standing position stand 302. In addition, for example, upon detecting that the radiation image capturing apparatus 300 is connected to the connector of the standing position stand 302 and is connected to the radiation image capturing apparatus communication cable 307, the attachment detection unit 305 may detect that the radiation image capturing apparatus 300 is attached to the standing position stand 302. The connection of the radiation image capturing apparatus communication cable 307 may be detected by, for example, hardware using a cable connection detection signal or by detecting the establishment of a communication link. The establishment of a communication link may be implemented by periodical exchange of acknowledgement signals between the wired communication unit 303 of the radiation image capturing apparatus 300 and the communication controller 323 or by determining whether wired or wireless connection is used upon acquiring communicable band information from information at the time of link establishment. When power is externally supplied to the radiation image capturing apparatus 300 through the radiation image capturing apparatus communication cable 307 or the like, the attachment of the radiation image capturing apparatus 300 to the standing position stand 302 may be detected based on the supply of power to the radiation image capturing apparatus 300 through the connector of the standing position stand 302. Alternatively, the attachment detection unit 305 may detect the attachment of the radiation image capturing apparatus 300 to the standing position stand 302 by connecting the radiation image capturing apparatus 300 to a cooling device provided for the standing position stand 302 to cool the radiation image capturing apparatus 300. The number of attachment detection units 305 provided for the radiation image capturing apparatus 300 is not limited to one. A plurality of attachment detection units 305 may be provided for the radiation image capturing apparatus to detect, by a plurality of methods, whether the radiation image capturing apparatus 300 is attached to the standing position stand 302.

This embodiment has exemplified the case in which when receptor fields are limited, display on the display device 314 is used to allow the user 312 to understand usable receptor fields. However, this is not exhaustive. For example, the radiation image capturing apparatus 300 may further include a notification unit that notifies that the receptor field selected by the user 312 cannot be used when the selected receptor field is different from selectable receptor fields. The notification unit may be configured to display, on the display device 314, information indicating that a selected receptor field cannot be used or to notify the user 312 by a warning sound such as a buzzer sound. In addition, the notification unit may perform notification at, for example, the timing when a state change occurs and the setting of selectable receptor fields changes upon detachment of the radiation image capturing apparatus 300 from the standing position stand 302.

This embodiment has exemplified the case in which the selection unit 406 is provided for the radiation image capturing apparatus 300. However, this is not exhaustive. For example, the controller 310 may be equipped with the function of the selection unit 406. In this case, the "radiation image capturing apparatus" according to the present invention can be an apparatus including the radiation image capturing apparatus 300 and the function of the selection unit 406 of the controller 310.

Radiation image capturing apparatuses according to some embodiments of the present invention will be described with reference to FIGS. 9 to 11. The first embodiment described above has exemplified the case in which the attachment of the radiation image capturing apparatus 300 to the standing position stand 302 is detected by using the attachment detection unit 305 of the radiation image capturing apparatus 300. In contrast to this, the second embodiment will exemplify a case in which a communication controller 323 is used as a detection unit for detecting that a radiation image capturing apparatus 300 is attached to a standing position stand 302. That is, a radiation image capturing system 10 may further include one or more detection units for detecting that the radiation image capturing apparatus 300 is attached to the standing position stand 302 in addition to the radiation image capturing apparatus 300.

The radiation image capturing system 10 according to this embodiment may have an arrangement similar to that shown in FIG. 1, and hence a description of the arrangement will be omitted. Note, however, that the communication controller 323 according to the embodiment is provided with a plurality of ports for the connection of a radiation image capturing apparatus communication cable 307 to enable connection to a plurality of radiation image capturing apparatuses 300. In the case described below, three ports are prepared.

Figure 9:
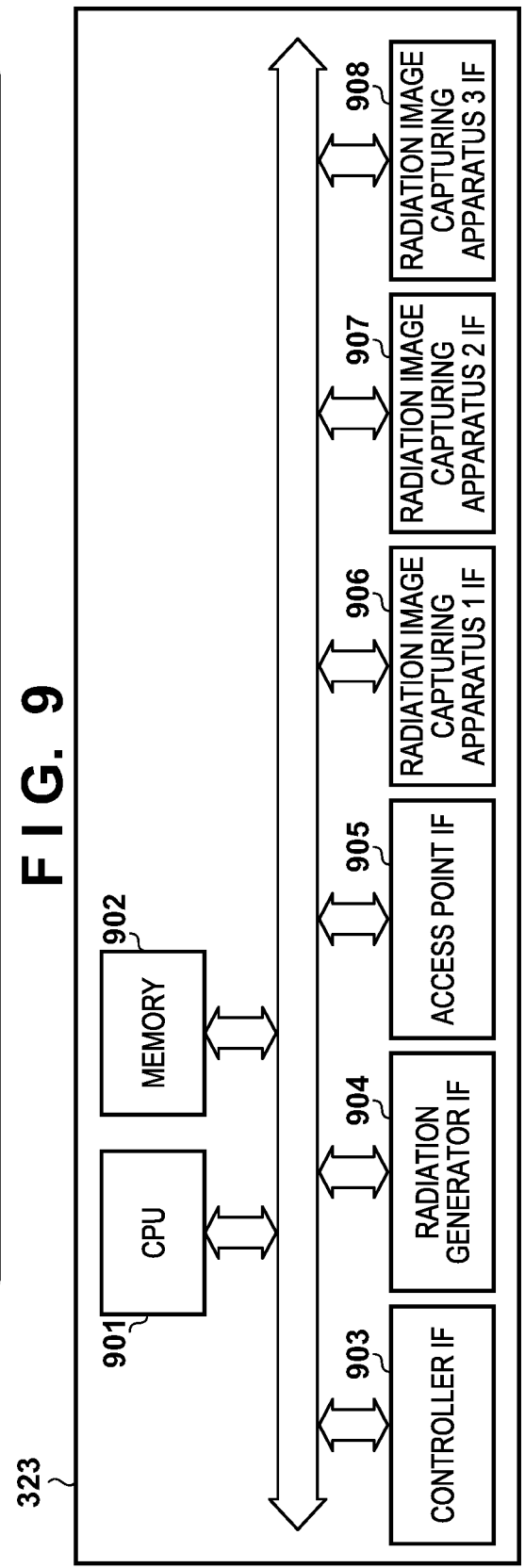
FIG. 9 is a block diagram showing an example of the arrangement of the control unit of the radiation image capturing apparatus in FIG. 1.

FIG. 9 shows an example of the arrangement of the communication controller 323 according to this embodiment. As shown in FIG. 9, the communication controller 323 includes a CPU 901, a memory 902, a controller IF 903, a radiation generator IF 904, an access point IF 905, a radiation image capturing apparatus 1 IF 906, a radiation image capturing apparatus 2 IF 907, and a radiation image capturing apparatus 3 IF 908.

The CPU 901 controls the overall communication controller 323 by using programs and various types of data stored in the memory 902. The memory 902 saves, for example, programs and various types of data used when the CPU 901 executes processing. The various types of data include, for example, settings for the respective interfaces of the communication controller 323. The controller IF 903, the radiation generator IF 904, and the access point IF 905 are respectively connected to the controller 310, the radiation generator 324, and the access point 320 through the radiation room communication cable 316, the radiation generator communication cable 327, and the access point communication cable 326 to communicate control signals, image data, and the like by using a communication device for a wired LAN such as Ethernet® and a public line. The radiation image capturing apparatus 1 IF 906, the radiation image capturing apparatus 2 IF 907, and the radiation image capturing apparatus 3 IF 908 all may have the same arrangement, and connect the radiation image capturing apparatus 300 to the radiation image capturing apparatus communication cable 307 to communicate control signals, image data, and the like by using a communication device for a wired LAN such as Ethernet® and a public line.

Figure 10:
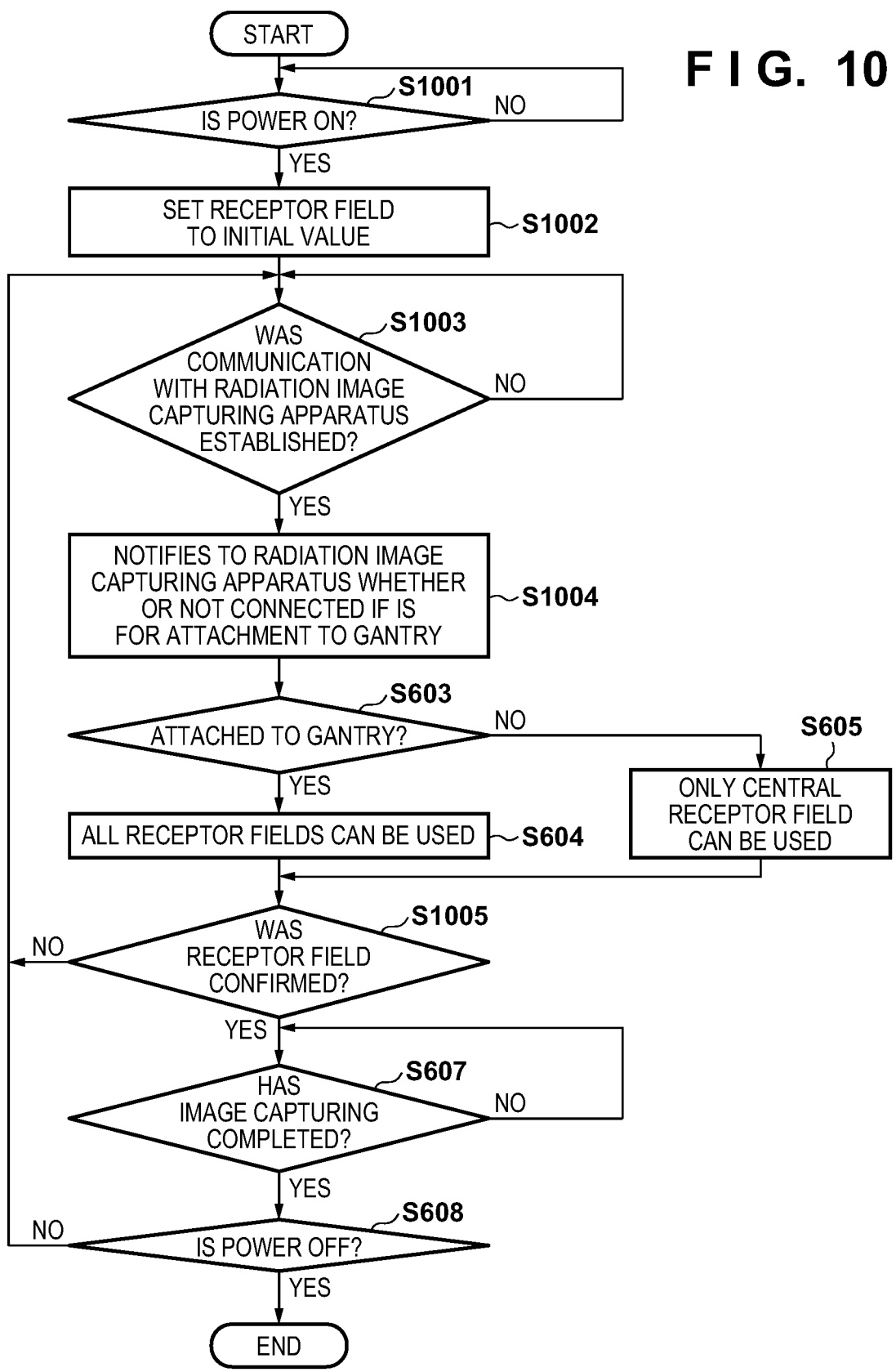
FIG. 10 is a flowchart showing processing at the time of image capturing by the radiation image capturing apparatus in FIG. 1.

FIG. 10 is a flowchart at the time of performing an image capturing operation using AEC control upon causing the communication controller 323 to detect whether the radiation image capturing apparatus 300 is attached to the standing position stand 302 (stand).

When the communication controller 323 is powered on upon powering on of the radiation image capturing system 10, the radiation image capturing system 10 shifts the process from step S1001 to step S1002. In step S1002, initialization is performed such that all the receptor fields in the radiation image capturing apparatus 300 are made settable.

The radiation image capturing system 10 then shifts the process to step S1003. The communication controller 323 detects whether the communication controller 323 and the radiation image capturing apparatus 300 are connected to any of the radiation image capturing apparatus 1 IF 906, the radiation image capturing apparatus 2 IF 907, and the radiation image capturing apparatus 3 IF 908 through the radiation image capturing apparatus communication cable 307. When a communication link is established between the communication controller 323 and the radiation image capturing apparatus 300, the radiation image capturing system 10 shifts the process to step S1004.

In step S1004, the communication controller 323 reads out information indicating whether the radiation image capturing apparatus IF in use is an IF for attachment to the stand from the setting information stored in the memory 902, and notifies the radiation image capturing apparatus 300 of the readout information. The radiation image capturing system 10 then shifts the process to step S603. In this case, for example, setting information indicating whether the IF in use is for attachment to the stand is set by a serviceman at the time of the installation of the radiation image capturing system 10, and is stored in, for example, the memory 902 in a table like that shown in FIG. 11. The setting information indicating whether the IF in use is for attachment to the stand may be changed as appropriate. When the information is changed, the communication controller 323 may notify the radiation image capturing apparatus 300 of the change at the timing when the information is changed. If the radiation image capturing apparatus IF used in step S1004 is an IF for attachment to the stand, it is possible to detect that the radiation image capturing apparatus 300 is attached to a stand like the standing position stand 302. That is, establishing a communication link between the communication controller 323 functioning as a detection unit and the radiation image capturing apparatus 300 through a predetermined stand (for example, the standing position stand 302) allows the communication controller 323 to detect whether the radiation image capturing apparatus 300 is attached to the stand. In this embodiment, when a radiation image capturing apparatus IF in use is confirmed from the setting information stored in the memory 902, whether the radiation image capturing apparatus 300 is attached to the stand is confirmed. Accordingly, as in the first embodiment described above, if the radiation image capturing apparatus 300 is attached to the stand (YES in step S603), the radiation image capturing system 10 shifts the process to step S604, in which the selection unit 406 makes all the receptor fields selectable. At this time, as shown in FIG. 7, the display device 314 displays that all the set receptor fields can be simultaneously used in one image capturing operation. The radiation image capturing system 10 then shifts the process to step S1005.

In step S603, if the radiation image capturing apparatus 300 is detached from the stand (NO in step S603), the radiation image capturing system 10 advances the process to step S605. In step S605, the selection unit 406 makes only the central receptor field selectable. The radiation image capturing system 10 then shifts the process to step S1005.

In step S1005, if the user 312 does not confirm the selection of a receptor field, the radiation image capturing system 10 returns the process to step S1003, and periodically repeats the processing from step S1003 to step S1005. In this manner, the radiation image capturing system 10 may periodically repeatedly determines by a polling scheme whether the radiation image capturing apparatus 300 is attached to the stand. Alternatively, the radiation image capturing system 10 may perform interrupt processing in response to a change in the state of a detection signal from the attachment detection unit 305. Control after the confirmation of a receptor field used for an image capturing operation using AEC control in step S1005 is similar to that in the first embodiment, and hence a description of the control will be omitted.

In this embodiment, when the communication controller 323 detects that the radiation image capturing apparatus 300 is not attached to the standing position stand 302, the radiation image capturing system 10 limits a usable receptor field to only the central receptor field of the radiation image capturing apparatus 300. This facilitates adjusting the positional relationship between an object and a receptor field as in the first embodiment. Accordingly, it is possible to provide the radiation image capturing apparatus 300 and the radiation image capturing system 10 which improve the usability for the user 312 and reduce the load in positioning the subject 306.

In the first embodiment, the radiation image capturing apparatus 300 detects whether the radiation image capturing apparatus 300 is attached to the standing position stand 302, whereas in the second embodiment, the communication controller 323 performs the same operation. However, this is not exhaustive. For example, at least one of a contact type sensor and a noncontact type sensor may be provided for a stand such as the standing position stand 302 and may function as a detection unit to detect whether the radiation image capturing apparatus 300 is attached to the stand. In addition, both the radiation image capturing apparatus 300 and the communication controller 323 and the stand each may be provided with a mechanism functioning as the attachment detection unit 305 or detection unit.

Other Embodiments

Embodiment(s) of the present invention can also be realized by a computer of a system or apparatus that reads out and executes computer executable instructions (e.g., one or more programs) recorded on a storage medium (which may also be referred to more fully as a non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2019-068067, filed on Mar. 29, 2019, which is hereby incorporated by reference herein in its entirety.

What is claimed is:

1. A radiation image capturing apparatus, comprising:
an image capturing unit configured to acquire a radiation image, the image capturing unit comprising a plurality of receptor fields configured to acquire irradiation information of radiation concerning an integrated dose of radiation entering during irradiation with radiation; and
a selection unit configured to select a receptor field that is used by a user, wherein
the selection unit is configured to change an upper limit of the number of receptor fields that are used for one image capturing operation depending on whether the radiation image capturing apparatus is attached to or detached from a stand to which the radiation image capturing apparatus can be attached.

2. The apparatus according to claim 1, wherein the selection unit is configured to greater reduce an upper limit of the number of receptor fields that are used for one image capturing operation when the radiation image capturing apparatus is detached from the stand than when the radiation image capturing apparatus is attached to the stand.

3. The apparatus according to claim 1, wherein the selection unit is configured to make a receptor field, of the plurality of receptor fields, which is arranged in a center of the image capturing unit selectable when the radiation image capturing apparatus is detached from the stand.

4. The apparatus according to claim 1, wherein the selection unit is configured to make all the plurality of receptor fields usable for one image capturing operation when the radiation image capturing apparatus is attached to the stand.

5. The apparatus according to claim 1, wherein the selection unit is configured to make one of the plurality of receptor fields selectable when the radiation image capturing apparatus is detached from the stand.

6. The apparatus according to claim 1, further comprising at least one attachment detection unit configured to detect whether the radiation image capturing apparatus is attached to the stand, wherein
the selection unit is configured to change an upper limit of the number of receptor fields that are used in accordance with a relationship between the radiation image capturing apparatus and the stand that is detected by the attachment detection unit.

7. The apparatus according to claim 6, wherein the attachment detection unit is configured to detect whether the radiation image capturing apparatus is attached to the stand using a contact or noncontact type sensor.

8. The apparatus according to claim 6, wherein the attachment detection unit is configured to detect that the radiation image capturing apparatus is attached to the stand when the radiation image capturing apparatus is connected to a connector provided for the stand.

9. The apparatus according to claim 8, wherein the attachment detection unit is configured to detect that the radiation image capturing apparatus is attached to the stand when the radiation image capturing apparatus is connected to the connector and a communication link is established between the radiation image capturing apparatus and an outside of the radiation image capturing apparatus through the connector.

10. The apparatus according to claim 8, wherein the attachment detection unit is configured to detect that the radiation image capturing apparatus is attached to the stand when the radiation image capturing apparatus is connected to the connector and power is supplied to the radiation image capturing apparatus through the connector.

11. The apparatus according to claim 8, wherein the attachment detection unit is congifured to detect that the radiation image capturing apparatus is attached to the stand when the radiation image capturing apparatus is connected to a cooling device provided for the stand and configured to cool the radiation image capturing apparatus.

12. The apparatus according to claim 1, further comprising an extraction unit configured to extract a receptor field for acquiring the irradiation information from the plurality of receptor fields, wherein
the extraction unit is configured to extract a selectable receptor field from the plurality of receptor fields in accordance with at least one of an image capturing region, an image capturing technique and an image capturing condition when the radiation image capturing apparatus is detached from the stand.

13. The apparatus according to claim 1, further comprising a notification unit configured to notify that a receptor field selected by a user from the plurality of receptor fields cannot be used when the selected receptor field is different from selectable receptor fields.

14. A radiation image capturing system, comprising:
the radiation image capturing apparatus according to claim 1; and
the stand.

15. The system according to claim 14, further comprising at least one detection unit configured to detect that the radiation image capturing apparatus is attached to the stand, wherein
the selection unit is configured to change an upper limit of the number of receptor fields that can be selected by the user in accordance with a relationship between the radiation image capturing apparatus and the stand that is detected by the detection unit.

16. The system according to claim 15, wherein the detection unit is configured to detect that the radiation image capturing apparatus is attached to the stand when a communication link is established with the radiation image capturing apparatus through the stand.

17. The system according to claim 15, wherein the detection unit detects whether the radiation image capturing apparatus is attached to the stand using a contact or non-contact type sensor provided for the stand.

18. A radiation image capturing apparatus, comprising:
an image capturing unit configured to acquire a radiation image, the image capturing unit comprising a plurality of receptor fields configured to acquire irradiation information of radiation concerning an integrated dose of radiation entering during irradiation with radiation; and
a selection unit configured to select a receptor field that is used, wherein
the selection unit is configured to change the number of receptor fields that are used for one image capturing operation depending on whether the radiation image capturing apparatus is attached to or detached from a gantry to which the radiation image capturing apparatus can be attached.

19. A radiation image capturing system, comprising:
a radiation image capturing apparatus including an image capturing unit configured to acquire a radiation image, the image capturing unit comprising a plurality of receptor fields configured to acquire irradiation information of radiation concerning an integrated dose of radiation entering during irradiation with radiation;
a gantry to which the radiation image capturing apparatus can be attached; and
a controller including an input device configured to select a receptor field that is used by a user, wherein
the controller is configured to change the number of receptor fields that are used for one image capturing operation depending on whether the radiation image capturing apparatus is attached to or detached from the gantry.

20. The system according to claim 19, wherein the gantry comprises a fluoroscopic or supine position table.

* * * * *